United States Patent [19]
Greve

[11] Patent Number: 5,917,590
[45] Date of Patent: Jun. 29, 1999

[54] OPTICAL INSPECTION DEVICE AND LITHOGRAPHIC APPARATUS PROVIDED WITH SUCH A DEVICE

[75] Inventor: Peter F. Greve, Eindhoven, Netherlands

[73] Assignee: U.S. Philips Corporation, New York, N.Y.

[21] Appl. No.: 08/944,908

[22] Filed: Oct. 6, 1997

[30] Foreign Application Priority Data

Dec. 24, 1996 [EP] European Pat. Off. ............. 96203735

[51] Int. Cl.[6] .................................................. G01N 21/47
[52] U.S. Cl. .................................. 356/237.3; 250/559.48
[58] Field of Search ............................. 356/237, 237.2, 356/237.3, 237.4; 250/559.48, 201.3, 201.6

[56] References Cited

U.S. PATENT DOCUMENTS 3,790,287  2/1974  Cuthbert et al. ....................... 356/237
4,686,359  8/1987  Yokoi et al. .......................... 250/201.3
5,359,407  10/1994 Suzuki et al. .......................... 356/237

FOREIGN PATENT DOCUMENTS

0658810A1  6/1995  European Pat. Off. .
06034557    2/1994  Japan .

*Primary Examiner*—Richard A. Rosenberger
*Attorney, Agent, or Firm*—Daniel E. Tierney

[57] ABSTRACT

A description is given of an optical inspection device for inspecting two oppositely located surfaces (3, 4) of a transparent object (1), for example a lithographic mask. The device is constructed in such a manner that for each inspection beam (a, c) the radiation path to the surface to be inspected (3, 4) is substantially equal to the radiation path from the surface to be inspected to a detector (29, 40), so that these paths comprise the same scanning element (10), preferably a mirror polygon. By virtue thereof, the radiation spots formed on the detectors are stationary and an inspection signal having a good signal-to-noise ratio is obtained.

11 Claims, 5 Drawing Sheets

OPTICAL INSPECTION DEVICE AND LITHOGRAPHIC APPARATUS PROVIDED WITH SUCH A DEVICE

The invention relates to an optical inspection device for inspecting a first surface and an oppositely located second surface of an object by means of, respectively, a first and a second inspection beam, the path of each inspection beam extending from a radiation source via a number of optical elements for guiding the relevant inspection beam to, and focusing the beam on, the surface to be inspected, and this path being provided with a scanning element for moving a radiation spot formed by the inspection beam on the surface to be inspected across this surface, and a radiation-sensitive detector being present for each inspection beam, which serves to convert radiation from the inspection beam which is scattered by the surface to be inspected into an electric signal.

The invention also relates to a mask-inspection device and to a lithographic apparatus comprising said inspection device.

In U.S. Pat. No. 5,359,407, a description is given of a surface-inspection device which is used in the optical lithographic technique to manufacture, for example, semiconductor circuits (ICs). For this purpose, use is made of a photolithographic apparatus, a wafer stepper or a wafer step-and-scanner comprising a mask table, a projection-lens system and a substrate table. By means of the wafer stepper, a mask which is provided in the mask table and which has a first pattern is imaged on a reduced scale in a first IC area of a substrate which carries a photo-sensitive layer and which is provided in the substrate table. Subsequently, the substrate is displaced relative to the projection-lens system and the mask in such a way that a second IC area is situated under the lens system, and the mask pattern is imaged on this second IC area. This process is continued until the mask pattern is imaged on all IC areas of the substrate. Subsequently, the illuminated substrate is removed from the wafer stepper in order to be developed, etched and subjected to further treatments. This substrate is then provided with a new photo-sensitive layer and introduced again into the same or another wafer stepper where it is illuminated with a second mask pattern.

The details of the patterns which can be formed in a substrate by means of a wafer stepper have line widths of the order of 0.5 micron or less. Therefore, foreign particles, such as dust particles, in the imaging path can have a disastrous effect on the images if the size of these particles is not substantially smaller than the diameter of the imaging beam. Consequently, care must be taken to ensure that the interior of the apparatus itself, but also the substrates introduced into the apparatus are substantially dust-free. It is even more important that the masks are dust-free, because a dust particle on a mask pattern will disturb the image on all IC areas of the substrate, so that all ICs formed on this substrate exhibit the same defect. As the details in the mask pattern are only a factor of, for example, four or five larger than those in the substrate, dust particles on the mask pattern have a great influence on the images formed in the substrate. As a result, it is desirable to inspect the masks for dust particles and other impurities before they are arranged on the mask table. This requires a very accurate and reliable inspection device.

The mask comprises a transparent substrate having a properly polished upper side and a mask pattern, for example a chromium pattern, on the lower side. This pattern is meticulously inspected beforehand for dust particles whose dimensions range from small to very small, of the order of 0.1 micron, and then covered with a transparent protective layer in the form, for example, of a foil. Coarser dust particles may have deposited on this foil and on the upper side of the mask before the mask is introduced into the apparatus, so that both said upper side and the foil must be inspected. For this purpose, two scanning inspection beams are used, one of which is directed at the upper side of the mask and the other is directed at the foil.

As described in U.S. Pat. No. 5,359,407, to inspect a mask surface, a small radiation spot can be moved across the entire mask pattern, and a dust particle can be detected by means of a radiation-sensitive detector which is arranged such that it can receive radiation from said spot which has been scattered by a dust particle. To inspect the entire surface of the mask, a scanning radiation beam which scans the pattern in a first direction is used in combination with the movement of the mask in a second direction at right angles to the first direction. The two sides of the mask are inspected by means of two scanning inspection beams. These beams are moved across the two surfaces by means of a common scanning element in the form of a mirror polygon. The use of a common scanning element has the advantage that the device can be embodied so as to be smaller and cheaper.

In the inspection device described in U.S. Pat. No. 5,359,407, detection units are situated close to the surfaces to be inspected. Each one of these units comprises a lens, a diaphragm aperture on which the radiation received by the lens is concentrated, a fiber which is arranged so as to engage the diaphragm aperture, and, at the other end of the fiber, a detector in the form of a photomultiplier tube. In order to be able to detect scattered radiation from all points on the scanning line, the lens and the detector must be relatively large. In such systems, use is preferably made of a semiconductor detector. The relatively large size of such a detector would cause the inspection signal supplied by this detector to have an unfavorable signal-to-noise ratio.

It is an object of the invention to provide an inspection device which is compact and hence can suitably be built into an apparatus, and which enables detection to be performed at a good signal-to-noise ratio. This inspection device is characterized in that for each inspection beam there is first of all provided, in the path of said scattered radiation, an element which causes this radiation to traverse the same path, yet in the opposite direction, with the same optical elements as the inspection beam as far as the scanning element, and in that the detector is arranged behind this scanning element.

As the scattered radiation on its path to the detector is also reflected by the scanning element, the radiation spot formed on the detector stands still relative to this detector. This enables the detector to be of small dimensions, of the order of magnitude of the radiation spot, so that the desired, favorable signal-to-noise ratio is achieved. For guiding the scattered radiation to the mirror polygon, the same optical elements are used as for guiding from the mirror polygon and focusing the inspection beam, so that the device can be embodied so as to be more compact.

It is noted that in the English-language abstract of Japanese patent application 6-34557, a description is given of a surface-inspection device in which a radiation beam originating from the surface to be inspected follows the same path, up to a scanning element, as the inspection beam. In this device, the beam originating from the surface is a specularly reflected beam of the same cross-section as the inspection beam. In addition, this device is suitable only for scanning one surface of an object.

The inspection device in accordance with the invention is preferably further characterized in that a common scanning element is provided in the path of both inspection beams.

By virtue thereof, one more scanning element and the associated driving means can be dispensed with, thus enabling a more compact construction of the device. The scanning element may be, for example, an oscillating mirror, but it is preferably a mirror polygon, which has the advantage, relative to an oscillating mirror, that the useful scanning time per scanning period is greater.

A first embodiment of the inspection device, in which the scanning element is a mirror polygon, is characterized in that for each inspection beam there is a separate radiation source and a separate detector, and in that the inspection beams are incident on opposite mirror faces of the mirror polygon.

A preferred embodiment of the device, in which the scanning element is a mirror polygon, is characterized in that the two inspection beams are incident on the same mirror face of the mirror polygon.

As a result, the optical elements for both beams are situated substantially on one side of the mirror polygon, which enables a more compact design to be achieved.

The optical inspection device can further be characterized by a single radiation source and a beam splitter which is arranged between this source and the scanning element and which serves to form the two inspection beams from the radiation beam supplied by the source.

This embodiment can be further characterized in that a beam interrupter is arranged between the beam splitter and the scanning element, which beam interrupter serves to alternately block the two inspection beams.

Only one inspection beam at a time scans the associated surface, so that crosstalk between these beams cannot take place, i.e. the detector associated with one of the surfaces does not receive radiation from the inspection beam used to inspect the other surface.

To ensure that the scanning line generated by each of the inspection spots is a straight line, the inspection device is characterized in that, for each inspection beam, the radiation source is arranged relative to the scanning element in such a manner that the chief ray of the inspection beam reflected by this element extends at right angles to the axis of rotation of this element.

During inspection of the two surfaces of an object, for example a lithographic mask, the distance between a surface to be inspected and the optical elements which are very near this surface is a critical parameter. If this distance is unequal to the desired distance, a portion of the radiation which is specularly reflected or deflected by a dust-free area of the surface may be incident on the detector, causing this detector to give a wrong signal. To eliminate the risk of an erroneous indication, the inspection device is further characterized in that it comprises an optical altimeter which includes a radiation-source unit for supplying a converging measuring beam whose chief ray makes a first angle with the normal to the first surface, and a position-sensitive detection unit for detecting a radiation beam reflected by the first surface whose chief ray makes a second angle with said normal, which angle is opposed to the first angle.

The signal from the altimeter can be used, for example, to correct the height of the mask.

If the inspection device is intended for inspecting a transparent object, the altimeter is preferably further characterized in that it comprises a diaphragm which is oriented and positioned such that only the radiation beam reflected by the first surface can pass through the diaphragm aperture and reach the detection unit, while a radiation beam reflected by the second surface is blocked by the diaphragm.

By virtue of this measure, it is precluded that radiation which is reflected by the lower side of the object can reach the detector and influence the height-measuring signal. This is particularly important if the object is a transparent mask, the mask pattern is situated on the lower side of the mask and this pattern is formed by linear apertures in a properly reflecting layer, such as a chromium layer.

The invention also relates to a lithographic apparatus for imaging a mask pattern on a substrate, which apparatus comprises an illumination system, a mask table for accommodating a mask and a substrate table for accommodating a substrate. This apparatus is characterized in that the above-mentioned mask-inspection device is arranged in the mask-supply path to the mask table.

These and other aspects of the invention will be apparent from and elucidated with reference to the embodiments described hereinafter.

Figure 1:
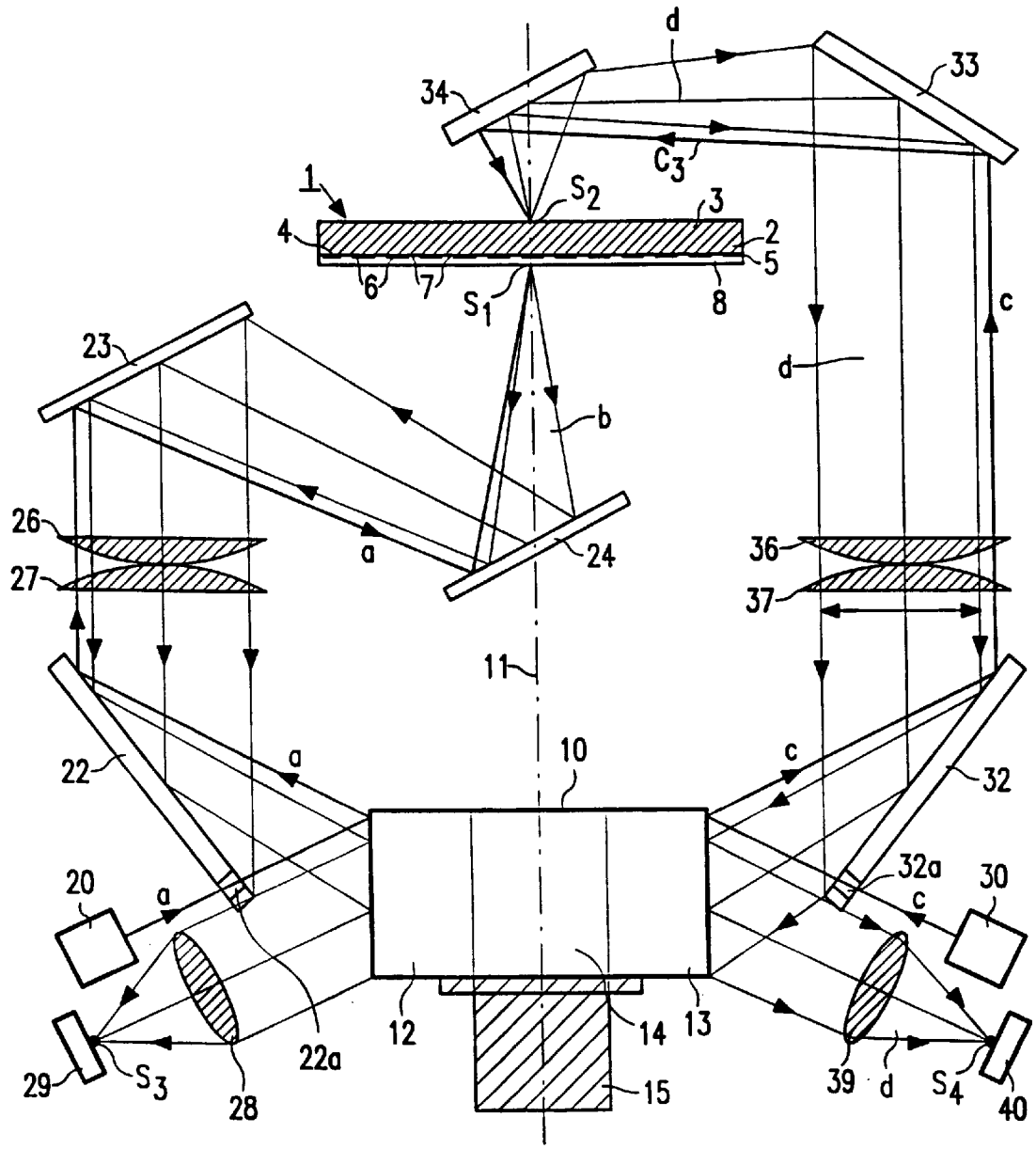
FIG. 1 is a first embodiment of a mask-inspection device.

In FIG. 1, reference numeral 1 indicates a lithographic mask. This mask comprises a transparent, for example glass, substrate 2 having an upper side 3 and a lower side 4. Said lower side is provided with a mask pattern 5 which is formed by a two-dimensional pattern of linear interruptions 7 in a non-transparent layer 6, which is generally made of chromium. This pattern is covered with a transparent foil 8.

To inspect the lower side of the mask formed by the foil 8, the inspection device comprises a first radiation source 20, preferably a diode laser, which emits a radiation beam a towards a scanning element. In this embodiment, the scanning element is formed by a centrally arranged mirror polygon 10 which is driven by a motor 15. The mirror polygon includes a number of mirror faces, three of which, namely 12, 13 and 14, are shown in FIG. 1. One of said mirror faces is always present in the path of the inspection beam a. This mirror face reflects the beam a, and, owing to the movement of said mirror, the reflected beam is moved in a plane at right angles to the axis of rotation 11 of the polygon. In the case of an ongoing rotation of the mirror polygon, the beam is moved forward and backward. The moving inspection beam is reflected in the direction of the mask by a first reflector 22 which includes, for example, a hole 22a to allow passage of the beam originating from the radiation source 20. Via two further reflectors 23 and 24, the beam is guided to the lower side of the mask, i.e. the foil, so that said foil is illuminated with an inspection spot S1. A scanlens comprising, for example, two lenses 26, 27 is arranged in the path of the inspection beam. When the mirror polygon is rotated, the inspection spot moves linearly from left to right, and conversely, across the lower side 8 of the mask, so that said side is scanned in a first direction. To scan the entire surface 8, a second movement at right angles to the first linear movement is necessary. This can be achieved by moving the mask relative to the elements of the inspection device in a direction at right angles to the plane of drawing of FIG. 1.

As long as the scanning inspection spot does not meet a dust particle or irregularity in the surface 8, the incident inspection beam is specularly reflected, that is, the angle relative to the normal to the surface at which the inspection beam is reflected is equal to the angle at which the beam is incident on the surface. This angle is chosen to be such that no radiation from the reflected beam is received by the elements 24, 23, 26 and 27, so that no radiation of said beam can reach the detector. If, however, the inspection spot is incident on a dust particle, the radiation of the inspection beam is scattered; in this case, reflected radiation is incident on the reflector 24 and said radiation is guided, as radiation beam b, via the elements 23 and 22 to the mirror face which has reflected the inspection beam a. This mirror face reflects the beam to a detector 29, said beam being focused on the detector by a lens 28. As the beam b is reflected by the same mirror face as the beam a, the beam b reflected by this mirror face stands still in the space and the radiation spot S3 formed on the detector 29 is stationary relative to the detector. By virtue of this measure in accordance with the invention, the radiation-sensitive surface of the detector can be embodied so as to be small, that is, of the same order of magnitude as the spot S3. As a result, the risk that radiation other than that originating from beam b is incident on this detector is small, so that the output signal of this detector, which gives an indication about the presence of dust particles and other irregularities, has a good signal-to-noise ratio.

To inspect the upper surface 3 of the mask, the inspection device comprises a second radiation source 30, a second set of reflectors 32, 33, 34, a second scanlens 36, 37, a second lens 39 and a second detector 40. The second inspection beam c supplied by the radiation source 30, and the beam d of scattered radiation, which is formed if a dust particle is situated on the upper side of the mask at the location of the second inspection spot S2, are reflected by a mirror surface 13 of the polygon 10, which is situated opposite the mirror surface 12 which reflects the inspection beam a.

Figure 2:
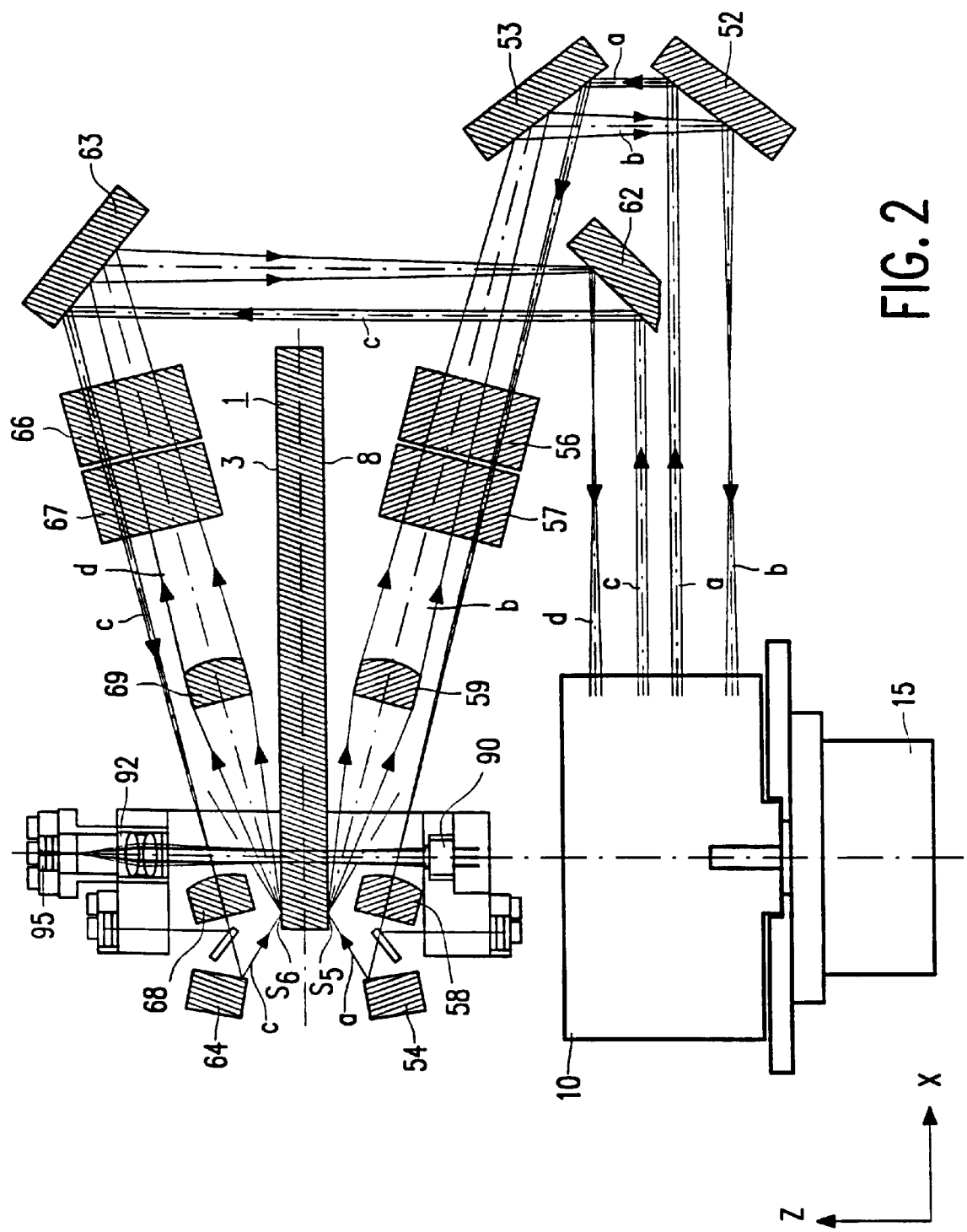
FIG. 2 shows a part of a preferred embodiment of this device.
Figure 3:
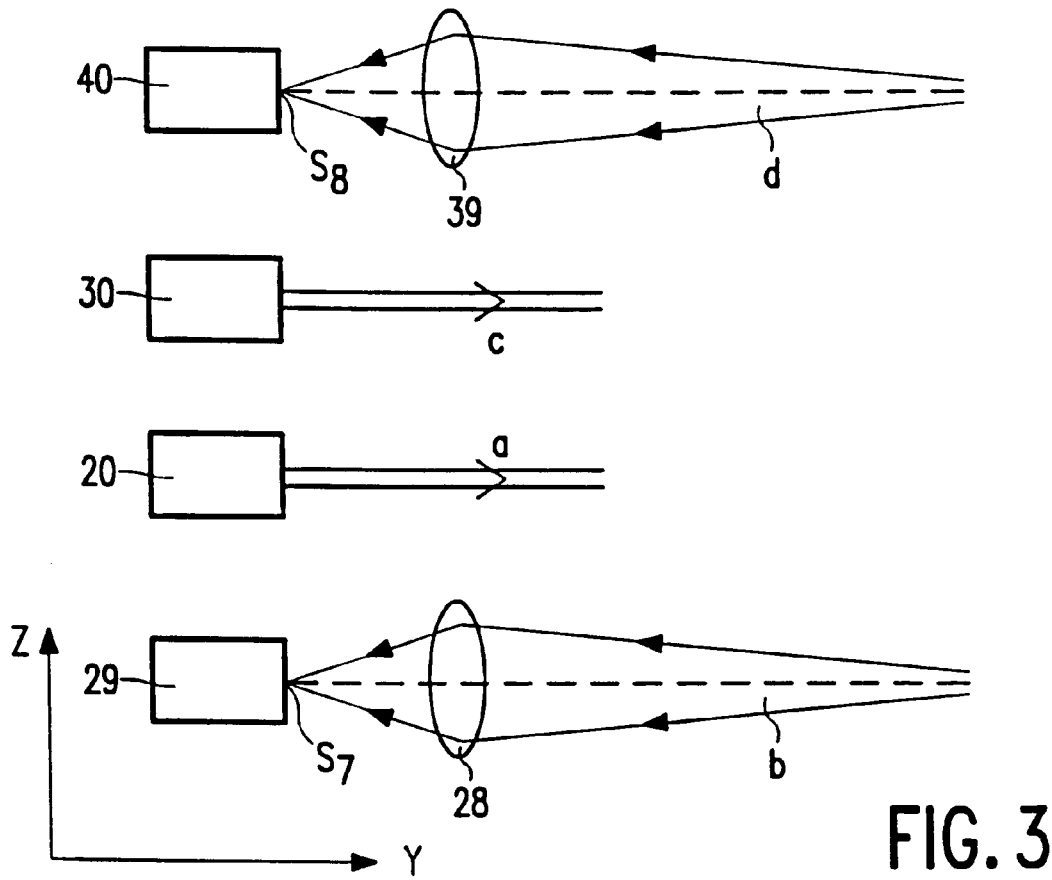
FIG. 3 shows another part of this embodiment.

FIGS. 2 and 3 show parts of a preferred embodiment of the inspection device. FIG. 2 shows a cross-sectional view in accordance with an XZ plane of an imaginary three-axis system of co-ordinates XYZ, and FIG. 3 shows a sectional view in a plane ZY at right angles thereto. FIG. 2 does not show the radiation sources and the detectors. These radiation sources 20, 30 and detectors 29, 40 are shown in FIG. 3. The inspection beams a, c supplied by the radiation sources are incident on the associated mirror faces of the mirror polygon 10 at such an angle that the chief rays of the inspection beams reflected by these faces extend in the plane of the drawing of FIG. 2. The inspection beam a reflected by the mirror polygon is guided to the lower side of the mask 1 via reflection at the reflectors 52, 53 and 54, and the reflected beam b of scattered radiation, which is formed if a dust particle is present on the lower side of the mask, is guided to the mirror polygon via reflection at the reflectors 53 and 52. The mirror polygon reflects the beam b to the detector 29, and the lens 28 forms the radiation spot S7 on the detector. The inspection beam C reflected by the mirror polygon is similarly guided to the upper side of the mask via reflection at the reflectors 62, 63 and 64, and the reflected beam d of scattered radiation which is formed if a dust particle is present on the upper side of the mask, is guided to the mirror polygon via reflection at the reflectors 63 and 62. The mirror polygon reflects the beam d to the detector 40, and the lens 39 forms the radiation spot S8 on this detector. A scanlens 56, 57 and a scanlens 66, 67 are provided in the path of the beams a, b and the beams c, d, respectively.

In the embodiment shown in FIGS. 2 and 3, for each inspection beam a lens 59 and a lens 69, respectively, are arranged close to the surface to be inspected by this beam. By virtue thereof, the amount of scattered radiation which is received and which can reach the relevant detector is increased. Preferably, in the path of each inspection beam, also a cylindrical lens 58 and a cylindrical lens 68, respectively, are arranged between the scanlens and the surface to be inspected. By virtue thereof, the quality of the inspection spot is constant throughout a scanning line. An elongated inspection spot S5 or S6, respectively, is formed on the surface to be inspected. If the embodiment comprises cylindrical lenses 58 and 68, then the lenses 59 and 69 are also cylindrical lenses.

Figure 4:
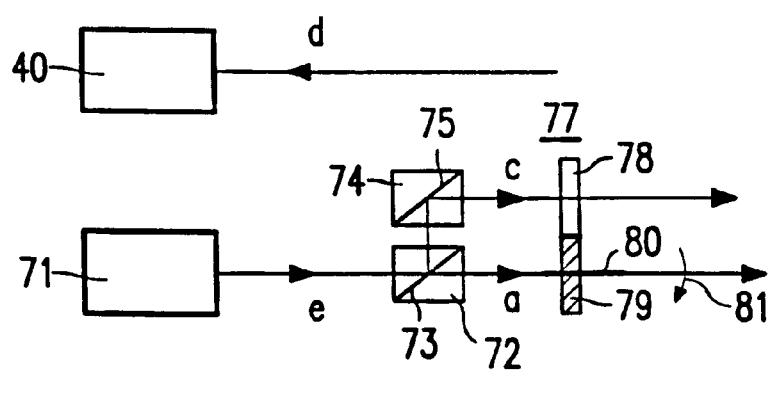
FIG. 4 shows an alternative to this other part.

As shown in FIG. 4, the two individual radiation sources can also be replaced by a combination of one radiation source and a beam splitter. In FIG. 4, the radiation source bears reference numeral 71. The beam e emitted by this source is split into an ongoing beam a and a reflected beam c by a partially, preferably semi-, transmitting mirror or a prism 72 having an internal, partially transmitting mirror face 73. A reflector 75 may be arranged in the path of the latter beam, which reflector reflects the beam c in such a manner that it extends parallel to the beam a.

The beams a and c traverse the inspection device in the manner shown in FIG. 2.

In the embodiment associated with FIGS. 2, 3 and 4, the inspection beams a and c are perpendicularly incident on the axis of rotation of the mirror polygon, which results in the advantage that the scanning lines formed by the inspection spots on the surfaces to be inspected are straight lines. In the embodiment associated with FIG. 1 as well as in the embodiment associated with FIG. 2, the number as well as the positions of the reflectors are chosen to be such that the optical paths are equal for both inspection beams.

In the above-described embodiments, the two radiation sources are preferably not switched on simultaneously, so that there is always only one inspection beam and either the upper side or the lower side of the mask is inspected. By virtue thereof, it is precluded that radiation from an inspection beam passing through the mask is incident on the detector associated with the other inspection beam. If a common radiation source is used to generate the two inspection beams, these beams can be switched by means of a beam chopper 77, as shown in FIG. 4. Said beam chopper comprises a round plate 77 one half 78 of which passes radiation and the other half 79 blocks radiation. The plate 77 can be rotated about an axis 80 in the direction indicated by the arrow 81. In the embodiment associated with FIG. 4, preferably, to switch the inspection beams, a swing-away reflector is arranged in the position of the beam splitter 72. By virtue thereof, the beam chopper 77 can be dispensed with and better use is made of the available radiation.

In the embodiment associated with FIG. 4, it would alternatively be possible to use only one detector. For this purpose, a further beam splitter can be arranged between the radiation source 71 and the beam splitter 72. This enables the common detector to be provided in the path of the radiation reflected by the further beam splitter. However, care must be taken that the surfaces of the optical elements are anti-reflecting.

Preferably, for each inspection beam, the lens system on the side of the surface to be inspected is constructed so as to be telecentric, that is, for each point within the inspection spot, the radiation is perpendicularly incident on the surface. By virtue thereof, it is precluded that radiation from the inspection beams which is incident on a side face of the mask can reach the detectors. A further advantage of said telecentricity is that a dust particle at the beginning or at the end of the scanning line generated by the inspection spot has the same effect as such a particle in the center of the scanning line, so that the detection accuracy is constant throughout the scanning line.

Instead of moving the mask in the inspection direction, scanning by means of the inspection spots in said second direction, at right angles to the scanning lines, can alternatively be carried out by arranging a second scanning element, for example an oscillating mirror or a second mirror polygon, in the path of each of the inspection beams. Also the second scanning element is arranged in the path of both the projected inspection beam and the reflected beam of scattered radiation, so that the radiation spot on the detector remains stationary.

It would also be possible to replace the mirror polygon 10 by an oscillating mirror. However, the advantage of a mirror polygon relative to a reciprocating flat mirror is that the retrace time for the inspection spot, that is, the time period between the end of a first scanning line and the beginning of a subsequent scanning line is shorter.

The inspection device may also comprise a presence-detection system for establishing whether the device comprises a mask and whether an inspection process must be started. As shown in FIG. 2, this detection system may be formed by a radiation source 90, for example an LED, which is situated on one side of the mask, and a detector 95, for example a photodiode, which is situated on the other side of the mask. In front of said detector there may be provided a lens system 92 comprising, for example, two lenses 93, 94, to form a radiation spot on the detector. The amount of radiation on the detector is determined by the presence or absence of a mask between the radiation source 90 and the detector 95.

Figure 5:
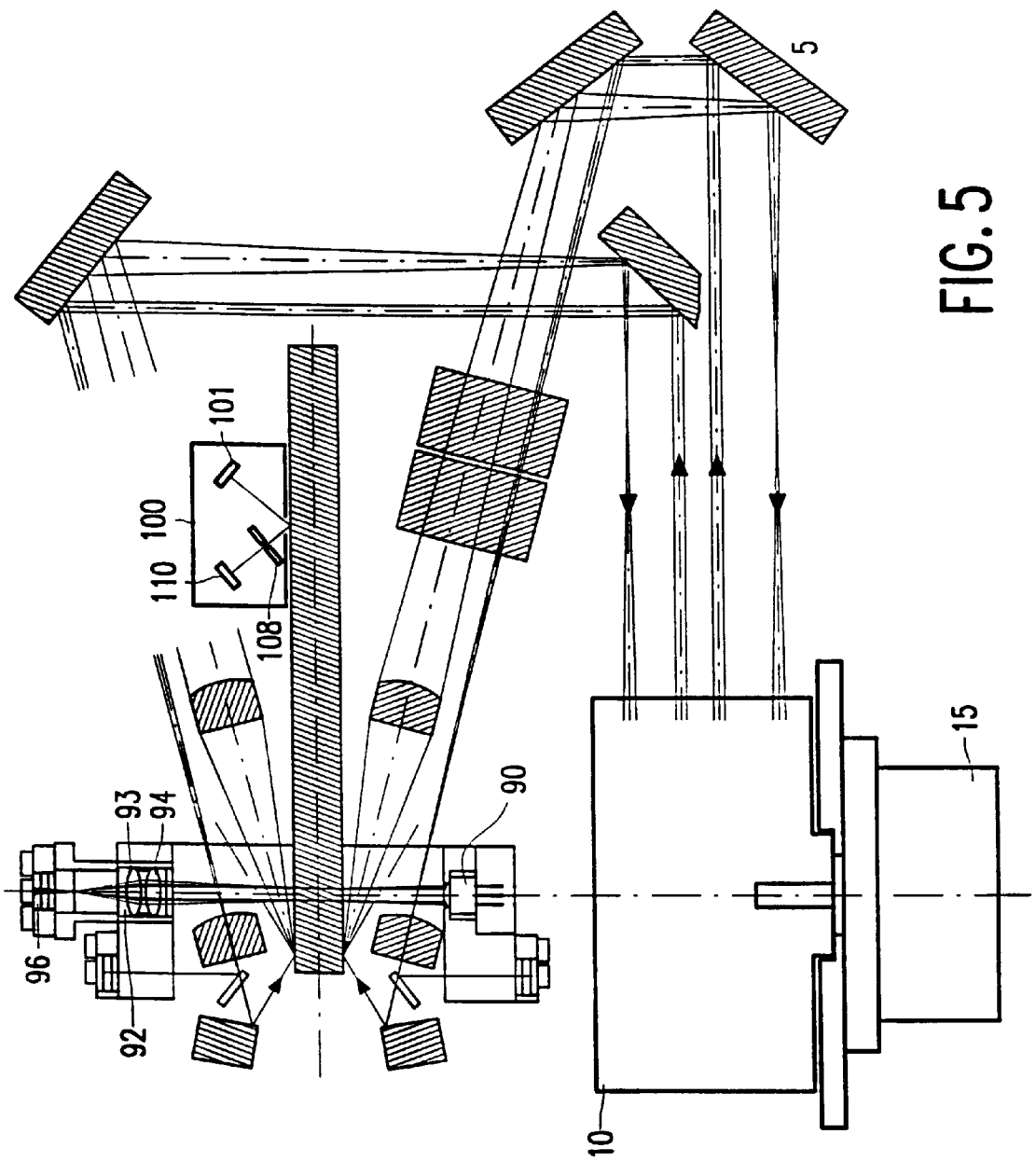
FIG. 5 shows an inspection device provided with an altimeter.
Figure 6:
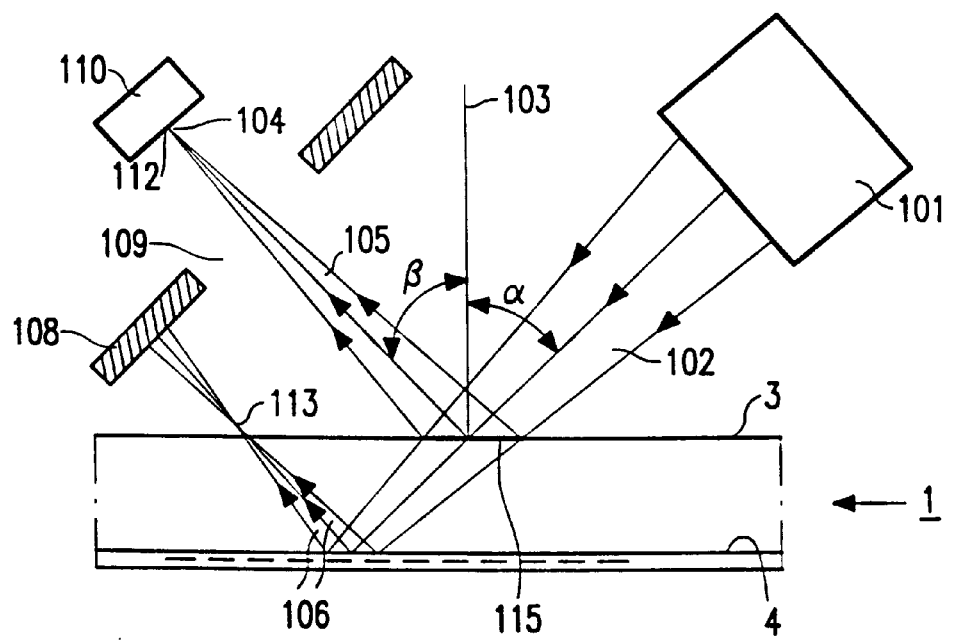
FIG. 6 shows the altimeter in detail.

The inspection device in accordance with the invention preferably comprises an altimeter to check the height of the upper side of the mask or another object. FIG. 5 shows an embodiment of the inspection device comprising an altimeter 100 which is constructed in a special manner to preclude that radiation from the measuring beam reflected by the lower side of the mask can influence the height-measuring signal from the altimeter. Apart from the altimeter 100, FIG. 5 shows the same inspection device as FIG. 2. In FIG. 5, however, a part of the inspection beam c and of the associated optical elements have been removed in order to show the altimeter. In practice, the altimeter is situated in front of or behind the plane of drawing of FIG. 2. FIG. 6 shows the altimeter in greater detail.

The altimeter 100 comprises a radiation-source unit 101 which is provided, for example, with a diode laser. Said unit 101 produces a converging measuring beam 102 which is incident at an angle α with the normal 103 on the upper side 3 of the mask. The measuring beam is specularly reflected by the surface 3, that is, the angle β at which the chief ray is reflected is equal, yet of opposite sense, to the angle of incidence α. The reflected measuring beam 105 is received by a detection unit 110 and forms a radiation spot 104 on the input face of said unit. The unit 110 comprises, for example, a position-sensitive photodiode or a CCD sensor. A change in height of the surface 3 brings about a change in position of the radiation spot 104 relative to the position-sensitive detector and hence also a change of the output signal of the detection unit. Thus, this output signal is a measure of the height of the surface 3. A part of the measuring beam radiation traverses the mask and can be reflected by the lower side of the mask. Without further measures, said reflected radiation 106 can reach the detection unit and cause a wrong height-measuring signal. This is likely to happen if the lower side 4 reflects more than the upper side 3, which occurs when use is made of a lithographic mask with a mask pattern on the lower side, which pattern is formed by a chromium layer with interruptions. To eliminate the risk of a wrong height-measuring signal, a diaphragm 108 is arranged between the upper side of the mask and the detection unit 110 such that the reflected measuring beam 105 passes through the diaphragm aperture 109 and reaches the detection unit. The radiation beam 106 reflected by the lower side 4 is blocked by the diaphragm and cannot reach the detection unit.

Unlike conventional height-measuring systems, the measuring beam 102 is not focused on the upper side of the mask, but instead the convergence of the beam is chosen to be such relative to the position of the diaphragm that, if the mask is at the desired height, the focus 112 of the reflected measuring beam 105 is situated behind the plane of the diaphragm and the focus 113 of the reflected radiation beam 106 is situated in front of the plane of the diaphragm. This results in a maximum capture range of the altimeter. Although the radiation spot 115 formed on the surface 3 by the measuring beam 102 is larger than that formed by a conventional altimeter, the risk that the height measurement is influenced by dust particles and other irregularities is substantially absent because the surface 3 is properly polished and exhibits the degree of dustlesness required for the height measurement itself.

To maximize the distance between the chief rays of the reflected beams 105 and 106 at the location of the diaphragm so as to ensure unobstructed passage of the beam 105 and proper blocking of the beam 106, the angle of incidence α is chosen to be of the order of 50°.

Further, the diameter of the diaphragm aperture 109 is preferably approximately equal to the distance between the chief rays of the beams 105 and 106. By virtue thereof, it is achieved that, also in the case of greater variations in height of the surface 3, the beam 105 passes through the aperture 109, while the beam 106 remains blocked.

If the surface 3 were tilted, the beam 105 would move towards the edge of the diaphragm aperture 109 and the beam 106 would move towards said aperture, thus causing the capture range of the altimeter to be reduced. To minimize the effect of a possible tilt, the diaphragm 108 is arranged as close to the radiation spot 115 as mechanically possible.

Figure 7:
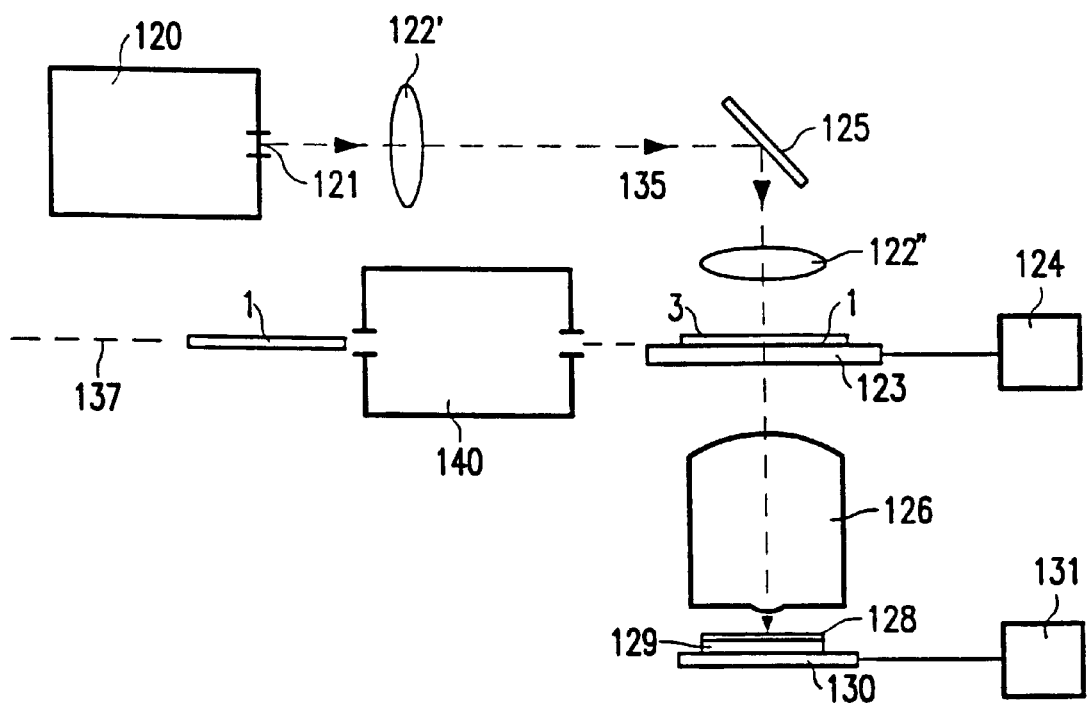
FIG. 7 shows a photolithographic projection apparatus provided with a mask-inspection device.

FIG. 7 very schematically shows the principle of an optical lithographic projection apparatus, in this case an apparatus of the scanning type, i.e. a mask 1 and a substrate 129 are moved in a projection beam synchronously while taking into account the magnification. Of this projection beam, only the chief ray is indicated by means of a dashed line 135. The apparatus can be used in the manufacture of micro-elements, such as integrated semiconductor circuits, liquid-crystalline display panels or magnetic heads.

The apparatus comprises a radiation source 120, for example an excimer laser, which emits a pulsed projection beam 135 via an exit window 121. Said exit window may be formed by the exit face of an optical integrator, such as a quartz rod, which enables the intensity to be uniformly distributed over the exit window, as described in EP patent application 0.658.810. A scanning lithographic apparatus preferably has an elongated exit window. This window is imaged on the mask 1 by a lens system 122 which comprises, for example, two lenses 122', 122", and which may be a telescopic system. The mask is provided on a mask table 123 which is driven by an actuator 124. The drive is such that the entire mask pattern is scanned with the image of the exit window. The longitudinal direction of the exit-window image extends at right angles to the scanning direction, i.e. the direction in which the mask 1 is moved by the actuator 124.

A projection-lens system 126, schematically indicated by a single lens in FIG. 7, images the illuminated portion of the mask pattern in a radiation-sensitive layer 128 on a substrate 129. This substrate may be a semiconductor wafer. The projection-lens system has a magnification, for example, of ¼. The substrate 129 is provided on a substrate table 130 which is driven by an actuator 131. When the mask pattern is imaged, the substrate and the mask are moved synchronously, while taking into account the magnification of the projection system 126, so that a series of adjacent images of the successively illuminated portions of the mask pattern are formed on the substrate. A possible scanning procedure is described in the article: "Sub-micron 1:1 Optical Lithography" by D. A. Markle in the magazine "Semiconductor International", May 1986, pp. 137–142. After the mask pattern has been imaged completely and an IC region of the substrate has been written completely, the substrate is moved relative to the mask over a distance which is slightly greater than an IC region, and the mask pattern is imaged on a subsequent IC region, etc., until all IC regions of the substrate have been provided with a mask-pattern image. To reduce the length of the apparatus, a folding mirror 125 may be arranged in the path of the projection beam.

To ensure that only highly dust-free masks are introduced into the projection column consisting of the elements 123, 126 and 130, the supply path of the masks, indicated by a dashed line 137, is provided with an optical mask-inspection device 140. This inspection device can be embodied as described with reference to the FIGS. 1–6.

The above-described inspection device can also be employed in an optical lithographic projection apparatus of the stepping-type. By means of such an apparatus, the mask pattern is always imaged in one shot on an IC region of the substrate. Subsequently, the substrate is moved relative to the mask, so that a subsequent IC region is situated under the mask and the lens system, and the mask pattern is imaged on this IC region. This process is repeated until all IC regions of the substrate are provided with a mask-pattern image. In a stepping-projection apparatus, the mask is not moved during the imaging process for an entire substrate and an actuator 124 is absent. The invention can also be employed in an optical lithographic apparatus which operates according to the proximity printing principle. Said apparatus does not comprise a projection-lens system, but instead the mask is arranged at a distance of the order of 1 micron from the substrate and a shadow image of the mask pattern is formed on the substrate. The inspection device in accordance with the invention can also be used in a lithographic apparatus in which a charged-particle beam, such as an ion beam, an electron beam or an X-ray beam is used as a projection beam. This type of apparatus, by means of which images can be formed whose details are even smaller than those formed by optical lithographic apparatus, must meet even higher requirements as regards freedom of dust of the masks, and an accurate and reliable inspection device is even more important.

The invention has been explained by means of a lithographic mask and a lithographic apparatus, however, this does not mean that the invention is limited thereto. The invention can also be employed in other systems for forming images having very small details, and, in general, its range of application includes all operations in which two opposing surfaces of a transparent object must be inspected.

I claim:

1. An optical inspection device for inspecting a first surface and an oppositely located second surface of an object by means of, respectively, a first and a second inspection beam, the path of each inspection beam extending from a radiation source via a number of optical elements for guiding the relevant inspection beam to, and focusing the beam on, the surface to be inspected, and this path being provided with a scanning element for moving a radiation spot formed by the inspection beam on the surface to be inspected across this surface, and a radiation-sensitive detector being present for each inspection beam, which serves to convert radiation from the inspection beam which is scattered by the surface to be inspected into an electric signal, characterized in that for each inspection beam there is first of all provided, in the path of said scattered radiation, an element which causes this radiation to traverse the same path, yet in the opposite direction, with the same optical elements as the inspection beam as far as the scanning element, the optical element positioned such that radiation from the inspection beam which is reflected by the surface to be inspected is not incident thereon and the reflected radiation is not caused to traverse the same path, yet in the opposite direction, with the same optical elements as the inspection beam, and in that the detector is provided behind this scanning element.

2. An optical inspection device as claimed in claim 1, characterized in that a common scanning element is provided in the path of both inspection beams.

3. An optical inspection device as claimed in claim 2, wherein the scanning element is a mirror polygon, characterized in that for each inspection beam there is a separate radiation source and a separate detector, and in that the inspection beams are incident on opposite mirror faces of the mirror polygon.

4. An optical inspection device as claimed in claim 2, wherein the scanning element is a mirror polygon, characterized in that the two inspection beams are incident on the same mirror face of the mirror polygon.

5. An optical inspection device as claimed in claim 4, characterized by a single radiation source and a beam splitter which is arranged between this source and the scanning element and which serves to form the two inspection beams from the radiation beam supplied by the source.

6. An optical inspection device as claimed in claim 5, characterized in that a beam interrupter is arranged between the beam splitter and the scanning element, which beam interrupter serves to alternately block the two inspection beams.

7. An optical inspection device as claimed in claim 4, characterized in that, for each inspection beam, the radiation source is arranged relative to the scanning element in such a manner that the chief ray of the inspection beam reflected by this element extends at right angles to the axis of rotation of this element.

8. An optical inspection device as claimed in claim 1, for inspecting two opposing surfaces of a transparent object, characterized by an optical altimeter which includes a radiation-source unit for supplying a converging measuring beam whose chief ray makes a first angle with the normal to the first surface, and a position-sensitive detection unit for detecting a radiation beam reflected by the first surface whose chief ray makes a second angle with said normal, which angle is opposed to the first angle.

9. An optical inspection device as claimed in claim 8, characterized in that the altimeter comprises a diaphragm which is oriented and positioned such that only the radiation beam reflected by the first surface can pass through the diaphragm aperture and reach the detection unit, while a radiation beam reflected by the second surface is blocked by the diaphragm.

10. A mask-inspection device for detecting dust particles on and defects in a lithographic mask, which device is formed by an inspection device as claimed in claim 1.

11. A lithographic apparatus for imaging a mask pattern on a substrate, which apparatus comprises an illumination system, a mask table for accommodating a mask and a substrate table for accommodating a substrate, characterized in that a mask-inspection device as claimed in claim 10 is arranged in the mask-supply path to the mask table.

* * * * *